United States Patent
Sakuragi (10) Patent No.: US 11,335,002 B2
(45) Date of Patent: May 17, 2022

(54) DEVIATION DETECTION DEVICE, METHOD, AND PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 221 days.

(21) Appl. No.: 16/853,695

(22) Filed: Apr. 20, 2020

(65) Prior Publication Data

US 2020/0250827 A1 Aug. 6, 2020

Related U.S. Application Data (63) Continuation of application No. PCT/JP2018/037248, filed on Oct. 4, 2018.

(30) Foreign Application Priority Data

Oct. 31, 2017 (JP) .............................. JP2017-210164

(51) Int. Cl.
*G06T 7/00* (2017.01)
*G06T 7/73* (2017.01)
(Continued)

(52) U.S. Cl.
CPC ............ *G06T 7/0016* (2013.01); *A61B 6/032* (2013.01); *G06T 7/149* (2017.01); *G06T 7/74* (2017.01);
(Continued)

(58) Field of Classification Search
CPC ......... G06T 7/0016; G06T 7/74; G06T 7/149; G06T 11/005; G06T 2200/04;
(Continued)

(56) References Cited

U.S. PATENT DOCUMENTS 7,693,563 B2 * 4/2010 Suresh .................. G16H 20/40
600/407
9,424,642 B2 * 8/2016 Hamada ............... A61B 6/5217
(Continued)

FOREIGN PATENT DOCUMENTS

JP 2006087631 4/2006
JP 2011115562 6/2011
(Continued)

OTHER PUBLICATIONS

"International Search Report (Form PCT/ISA/210)" of PCT/JP2018/037248, dated Dec. 18, 2018, with English translation thereof, pp. 1-5.

(Continued)

*Primary Examiner* — Shefali D Goradia
(74) *Attorney, Agent, or Firm* — JCIPRNET (57) ABSTRACT

A first acquisition unit acquires stent regions from each of three-dimensional images. A second acquisition unit acquires blood vessel regions from each of the three-dimensional images. A positioning unit acquires a first positioning result by positioning the blood vessel regions for each of the three-dimensional images. A deviation information acquisition unit acquires deviation information indicating a deviation of a stent from a blood vessel between the three-dimensional images based on the stent regions for the three-dimensional images and a deformation vector which is the first positioning result.

10 Claims, 7 Drawing Sheets

(51) Int. Cl.
*G06T 7/149* (2017.01)
*A61B 6/03* (2006.01)
*G06T 11/00* (2006.01)

(52) U.S. Cl.
CPC ........ *G06T 11/005* (2013.01); *G06T 2200/04* (2013.01); *G06T 2207/10081* (2013.01); *G06T 2207/30101* (2013.01)

(58) Field of Classification Search
CPC . G06T 2207/10081; G06T 2207/30101; A61B 6/032
See application file for complete search history.

(56) References Cited

U.S. PATENT DOCUMENTS

| | | | |
|---|---|---|---|
| 10,043,269 B2 * | 8/2018 | Wang | G16H 50/20 |
| 10,140,700 B2 * | 11/2018 | Takahashi | A61B 5/0245 |
| 2006/0210147 A1 * | 9/2006 | Sakaguchi | G01C 11/06 |
| | | | 382/154 |
| 2007/0297657 A1 | 12/2007 | Mattes et al. | |
| 2011/0103666 A1 | 5/2011 | Ohishi | |
| 2011/0237938 A1 * | 9/2011 | Mizuno | G06T 7/187 |
| | | | 600/425 |
| 2012/0004529 A1 | 1/2012 | Tolkowsky et al. | |
| 2012/0004537 A1 | 1/2012 | Tolkowsky et al. | |
| 2014/0204124 A1 | 7/2014 | Auvray et al. | |
| 2016/0174945 A1 * | 6/2016 | Oh | A61B 8/4405 |
| | | | 382/131 |
| 2016/0180525 A1 | 6/2016 | Reynolds et al. | |
| 2016/0346042 A1 * | 12/2016 | Nomiyama | G06T 17/00 |

FOREIGN PATENT DOCUMENTS

| | | | |
|---|---|---|---|
| JP | 2013537444 | 10/2013 | |
| JP | 2014525308 | 9/2014 | |
| JP | 2016116843 | 6/2016 | |
| JP | 2017018457 | 1/2017 | |
| WO | WO-2017042068 A1 * | 3/2017 | ............... G06T 7/33 |

OTHER PUBLICATIONS

"Written Opinion of the International Searching Authority (Form PCT/ISA/237)" of PCT/JP2018/037248, dated Dec. 18, 2018, with English translation thereof, pp. 1-7.

* cited by examiner

DEVIATION DETECTION DEVICE, METHOD, AND PROGRAM

CROSS REFERENCE TO RELATED APPLICATIONS

The present application is a Continuation of PCT International Application No. PCT/JP2018/037248 filed on Oct. 4, 2018, which claims priority under 35 U.S.C. § 119(a) to Japanese Patent Application No. 2017-210164 filed on Oct. 31, 2017. Each of the above applications is hereby expressly incorporated by reference, in its entirety, into the present application.

BACKGROUND

Technical Field

The present disclosure relates to deviation detection device, method, and program for detecting a deviation of a structure included in a medical image such as a Computed Radiography (CT) image.

Related Art

An operation of placing a stent in an artery has been currently performed as a treatment for an aneurysm. The stent is placed at a position planned in advance immediately after such an operation, but movement and deformation of the stent may occur with the passage of time. There is a possibility that a blood flow to an aortic aneurysm occluded by the stent is resumed due to such movement and deformation of the stent from the position planned in advance. In a case where the stent is placed, the branch of a blood vessel is not blocked. However, there is a possibility that the branch of the blood vessel is blocked due to the movement and deformation of the stent.

Therefore, it is important to ascertain whether or not there are the aforementioned possibilities in advance by quantifying the amount of movement and the amount of deformation of the stent. However, since the blood vessel itself in which the stent is placed moves with the passage of time, the stent also moves together with the blood vessel. Thus, it is difficult to detect the amount of movement and the amount of deformation of the stent with respect to the blood vessel in some CT images having different imaging times with the passage of time.

Here, various methods for positioning blood vessels by using medical images having different imaging times have been proposed. For example, JP 2017-018457A proposes a method of positioning a coronary artery CT image and a delayed contrast CT image such that a position deviation between outer contours of the coronary artery CT image and the delayed contrast CT image is minimized in a case where a myocardial infarction portion is identified by performing image processing for generating a difference image by performing difference processing using the coronary artery CT image and the delayed contrast CT image. JP 2006-087631 A proposes a method of creating a difference image between images obtained by injecting a contrast agent before and after an operation for placing a stent by generating a third image obtained by positioning various portions displayed on a first image and a second image of a plurality of images continuously collected before and after the contrast agent is injected and generating a subtraction between the second image and the third image.

However, in the methods described in JP 2017-018457 A and JP 2006-087631 A, the position deviation of the blood vessel between the images with the passage of time is detected, but the amount of movement and the amount of deformation of the stent placed in the blood vessel are not detected. As described above, since the blood vessel itself in which the stent is placed moves with the passage of time, the stent also moves together with the blood vessel. Thus, it is difficult to detect the deviation including the amount of movement and the amount of deformation of the stent with respect to the blood vessel by using the medical images having different imaging times.

SUMMARY OF THE INVENTION

The present disclosure has been made in view of the aforementioned circumstances, and an object of the present disclosure is to detect a deviation of a structure included in a medical image such as a stent placed in a blood vessel.

A deviation detection device according to the present disclosure comprises a first acquisition unit that acquires a first region indicating a first structure as a deviation detection target between two medical images having different imaging times for the same test subject from each of the two medical images, a second acquisition unit that acquires a second region indicating a second structure moving in interconnection with the first structure from each of the two medical images, a positioning unit that acquires a first positioning result by positioning the second region for each of the two medical images, and a deviation information acquisition unit that acquires deviation information indicating a deviation of the first structure from the second structure between the two medical images based on the first region for each of the two medical images and the first positioning result.

The "deviation information" includes the amount of movement of the first structure and the amount of deformation of the first structure with respect to the second structure between the two medical images.

In the deviation detection device according to the present disclosure, the second acquisition unit may acquire a third region including the first structure and the second structure from each of the two medical images, and may acquire the second region by removing the first region from the third region in each of the two medical images.

In the deviation detection device according to the present disclosure, the positioning unit may acquire the first positioning result by non-rigid positioning.

In the deviation detection device according to the present disclosure, the deviation information acquisition unit may acquire a second positioning result by positioning the first region for each of the two medical images, and may acquire the deviation information by removing a component based on the first positioning result from the second positioning result.

In the deviation detection device according to the present disclosure, the deviation information acquisition unit may acquire the second positioning result by non-rigid positioning.

In the deviation detection device according to the present disclosure, the deviation information acquisition unit may deform the first region for one medical image of the two medical images based on the first positioning result, and may acquire the deviation information based on the first region for the other medical image of the two medical images and the deformed first region.

In the deviation detection device according to the present disclosure, the medical image may include a blood vessel on which a stent is placed, the first structure may be the stent, and the second structure may be the blood vessel.

In the deviation detection device according to the present disclosure, the positioning unit may acquire the first positioning result by positioning a core line of a blood vessel region which is a region of the blood vessel for each of the two medical images.

A deviation detection method according to the present disclosure comprises acquiring a first region indicating a first structure as a deviation detection target between two medical images having different imaging times for the same test subject from each of the two medical images, acquiring a second region indicating a second structure moving in interconnection with the first structure from each of the two medical images, acquiring a first positioning result by positioning the second region for each of the two medical images, and acquiring deviation information indicating a deviation of the first structure from the second structure between the two medical images based on the first region for each of the two medical images and the first positioning result.

There is provided a program causing a computer to execute the deviation detection method according to the present disclosure.

Another deviation detection device according to the present disclosure comprises a memory that stores a command causing a computer to execute, and a processor configured to execute the stored command. The processor executes processing for acquiring a first region indicating a first structure as a deviation detection target between two medical images having different imaging times for the same test subject from each of the two medical images, acquiring a second region indicating a second structure moving in interconnection with the first structure from each of the two medical images, acquiring a first positioning result by positioning the second region for each of the two medical images, and acquiring deviation information indicating a deviation of the first structure from the second structure between the two medical images based on the first region for each of the two medical images and the first positioning result.

According to the present disclosure, the first region indicating the first structure as the detection target of the deviation between the two medical images having different imaging times is acquired from each of the two medical images, and the second region indicating the second structure moving in interconnection with the first structure is acquired from each of the two medical images. The first positioning result is acquired by positioning the second region for each of the two medical images, and the deviation information indicating the deviation of the first structure from the second structure between the two medical images is obtained based on the first region for each of the two medical images and the first positioning result. Thus, it is possible to detect the deviation of the first region from the second region.

DETAILED DESCRIPTION OF EMBODIMENTS

Figure 1:
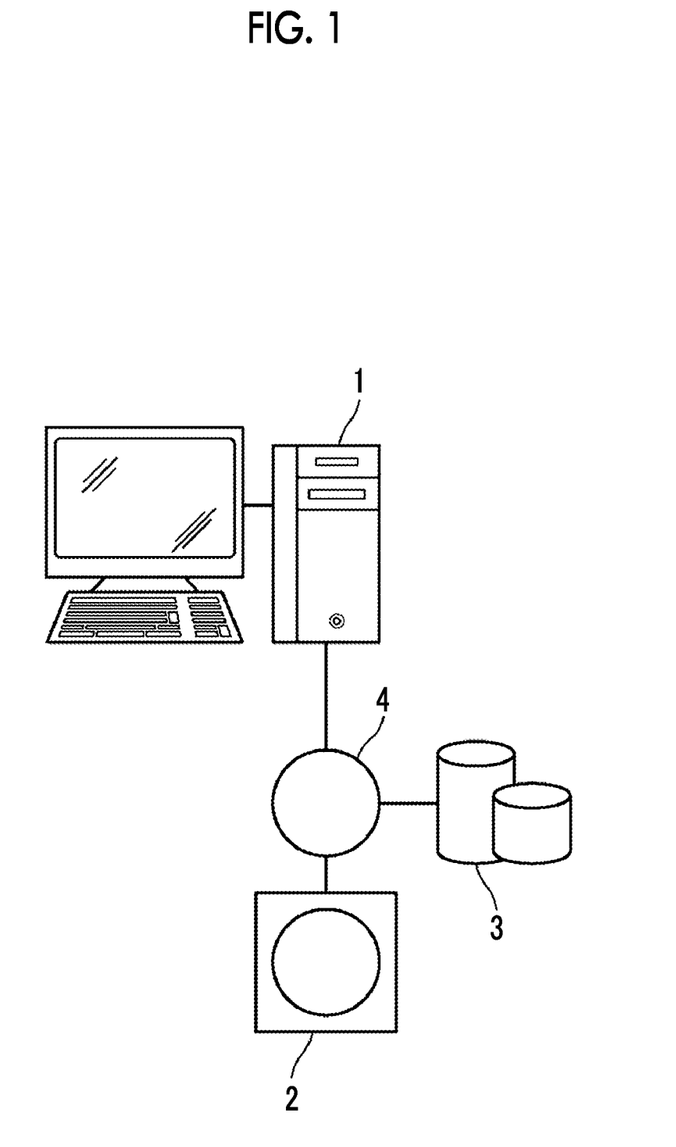
FIG. 1 is a hardware configuration diagram showing an outline of a diagnosis support system to which a deviation detection device according to an embodiment of the present disclosure is applied.

Hereinafter, an embodiment of the present disclosure will be described with reference to the drawings. FIG. 1 is a hardware configuration diagram showing an outline of a diagnosis support system to which a deviation detection device according to an embodiment of the present disclosure is applied. As shown in FIG. 1, in the diagnosis support system, a deviation detection device 1, a three-dimensional image imaging device 2, and an image storage server 3 according to the present embodiment are connected to be able to communicate via a network 4. In the diagnosis support system, processing for acquiring two three-dimensional images having different imaging times for a blood vessel such as an aorta in which a stent of a test subject is placed and detecting a deviation of the stent from the blood vessel between the two three-dimensional images is performed.

The three-dimensional image imaging device 2 is a device that images a three-dimensional image representing a diagnosis target part of the test subject to generate this part, and specifically, is a CT device, a Magnetic Resonance Imaging (MRI) device, or a Positron Emission Tomography (PET) device. The three-dimensional image generated by the three-dimensional image imaging device 2 is transmitted to the image storage server 3 and stored. In the present embodiment, since the deviation of the stent from the aorta is detected, the diagnosis target part of the test subject is the chest including the aorta. The three-dimensional image imaging device 2 is the CT device, and generates a three-dimensional image including a plurality of tomographic images of an axial section for the chest of the test subject. The three-dimensional image corresponds to a medical image.

The image storage server 3 is a computer that stores and manages various data, and includes a large-capacity external storage device and database management software. The image storage server 3 transmits and receives image data by communicating with other devices via a wired or wireless network 4. More specifically, the image data such as the three-dimensional image generated by the three-dimensional image imaging device 2 is acquired via the network, and is stored and managed in a recording medium such as a large-capacity external storage device. The storage format of the image data and the communication between the devices via the network 4 are based on a protocol such as Digital Imaging and Communication in Medicine (DICOM). In the present embodiment, a plurality of three-dimensional images for the same test subject having different imaging times is stored in the image storage server 3.

The deviation detection device 1 is a computer on which a deviation detection program according to the present disclosure is installed. The computer may be a workstation or a personal computer directly operated by a doctor who performs diagnosis, or a server computer connected to the workstation and the personal computer via the network. The deviation detection program is recorded and distributed on a recording medium such as a Digital Versatile Disc (DVD) or a Compact Disc Read Only Memory (CD-ROM), and is installed on the computer from the recording medium. Alternatively, the deviation detection program is stored in a storage device of a server computer connected to the network or a network storage in a state of being accessible from the outside, and is downloaded and installed on the computer used by the doctor according to a request.

Figure 2:
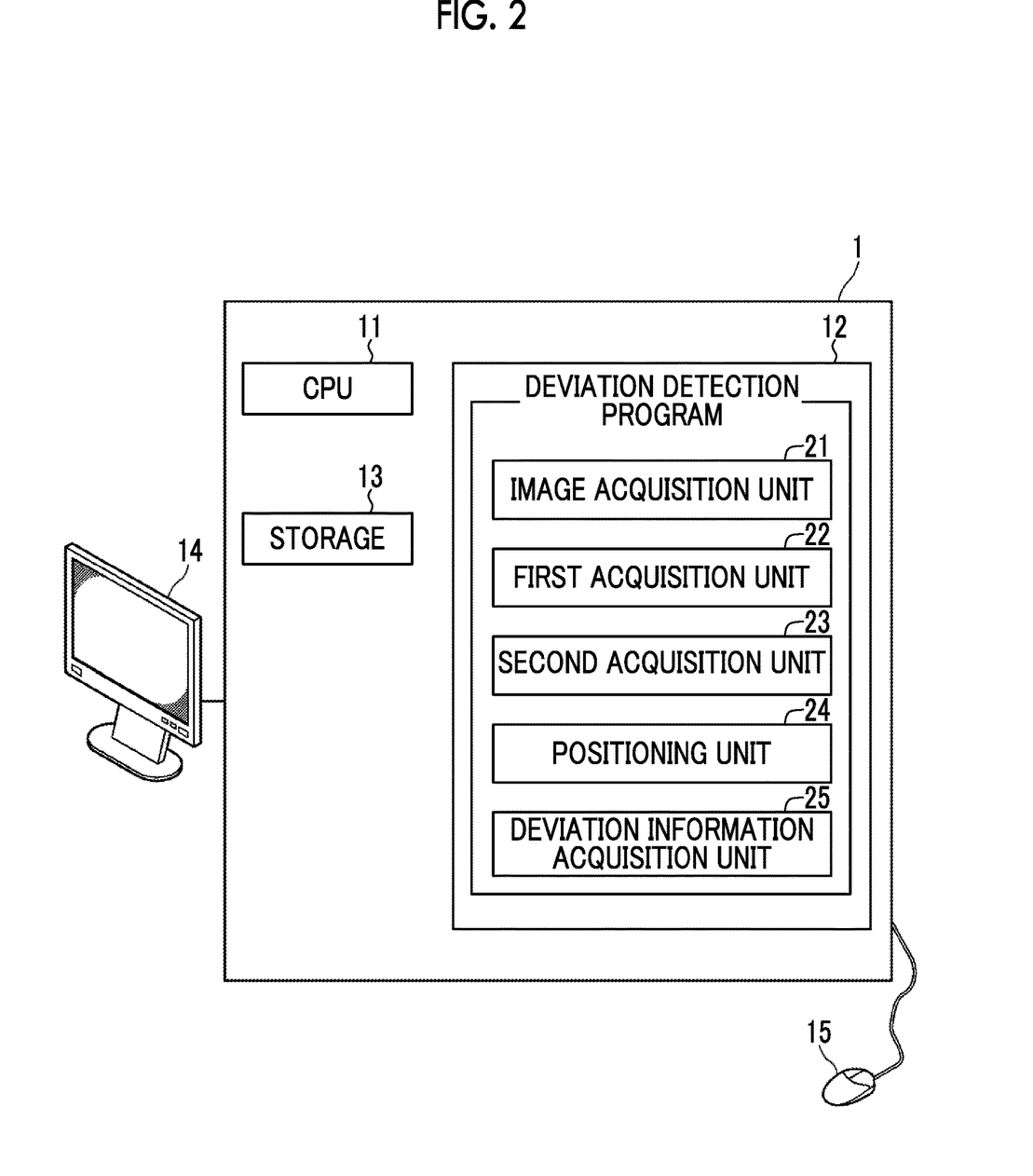
FIG. 2 is a diagram showing a schematic configuration of the deviation detection device.

FIG. 2 is a diagram showing a schematic configuration of the deviation detection device realized by installing the deviation detection program on the computer. As shown in FIG. 2, the deviation detection device 1 includes, as a configuration of a standard work station, a Central Processing Unit (CPU) 11, a memory 12, and a storage 13. A display 14 such as a liquid crystal display and an input unit 15 such as a keyboard and a mouse are connected to the deviation detection device 1.

The storage 13 includes a storage device such as a hard disk or a solid state drive (SSD). The storage 13 stores various types of information including the three-dimensional images of the test subject and information necessary for processing which are acquired from the image storage server 3 via the network 4.

The memory 12 stores the deviation detection program. The deviation detection program includes, first acquisition processing for acquiring a first region indicating a first structure as a detection target of the deviation between the two three-dimensional images from each of the two three-dimensional images having different imaging times for the same test subject, second acquisition processing for acquiring a second region indicating a second structure moving in interconnection with the first structure from each of the two three-dimensional images, positioning processing for acquiring a first positioning result by positioning the second region for each of the two three-dimensional images, and a deviation information acquisition processing for acquiring deviation information indicating a deviation of the first structure from the second structure between the two three-dimensional images based on the first region and the first positioning result for each of the two three-dimensional images are prescribed as processing to be executed by the CPU 11.

In a case where the CPU 11 executes these processing according to the program, the computer functions as an image acquisition unit 21, a first acquisition unit 22, a second acquisition unit 23, a positioning unit 24, and a deviation information acquisition unit 25. Although it has been described in the present embodiment that the function of each unit is executed by the deviation detection program, the present invention is not limited thereto. For example, the function of each unit may be executed by appropriately combining a plurality of Integrated Circuits (ICs), processors, Application Specific Integrated Circuits (ASICs), Field-Programmable Gate Arrays (FPGAs), and memories.

The image acquisition unit 21 acquires two three-dimensional images G1 and G2 having different imaging times for the same test subject from the image storage server 3. In a case where the three-dimensional images G1 and G2 are already stored in the storage 13, the three-dimensional images G1 and G2 may be acquired from the storage 13. In the following description, it is assumed that the imaging time of the three-dimensional image G1 is earlier than that of the three-dimensional image G2.

Figure 3:
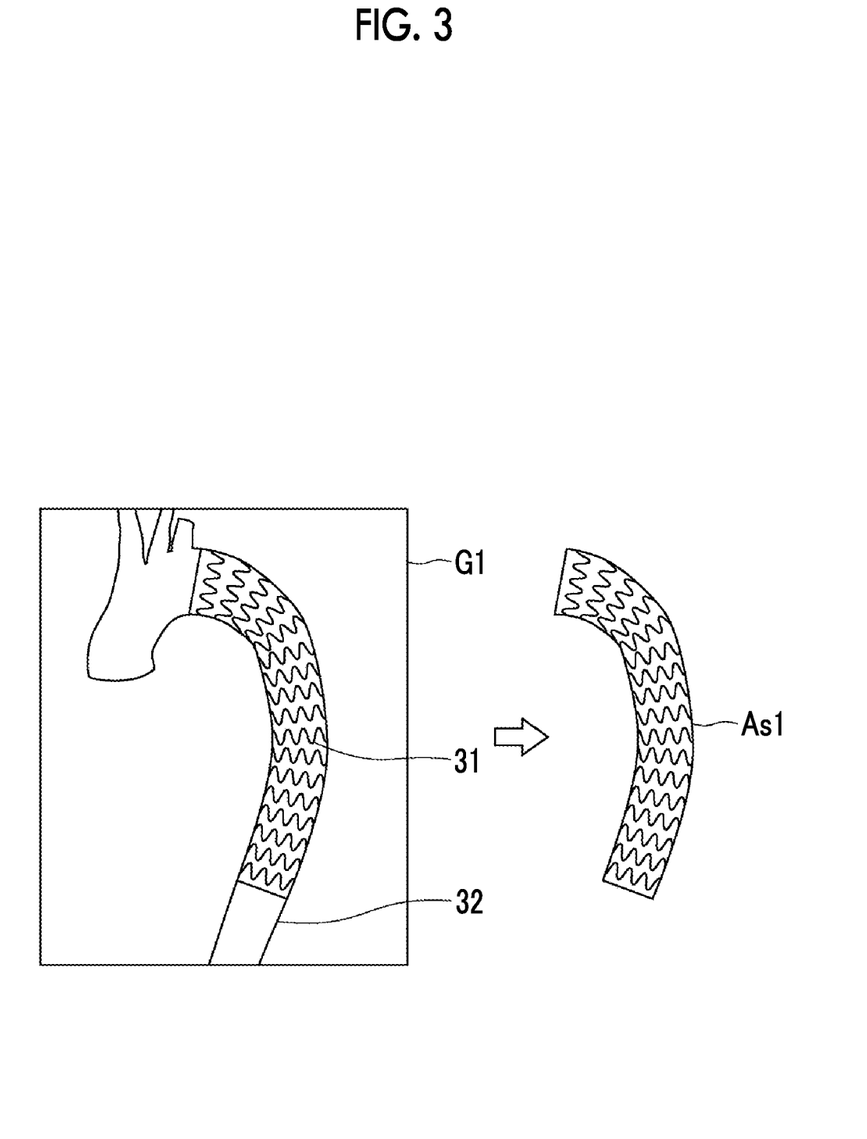
FIG. 3 is a diagram for describing acquisition of a stent region.

The first acquisition unit 22 acquires a stent region representing the stent as the detection target of the deviation between the two three-dimensional images G1 and G2 from each of the two three-dimensional images G1 and G2. The stent corresponds to the first structure, and the stent region corresponds to the first region. FIG. 3 is a diagram for describing the acquisition of the stent region. Since the acquisition of the stent region is performed by the same processing in the three-dimensional images G1 and G2, only the acquisition of the stent region from the three-dimensional image G1 will be described.

As shown in FIG. 3, the three-dimensional image G1 includes a blood vessel 32 on which a stent 31 is placed. Since the stent 31 is made of metal, the region of the stent 31 in the three-dimensional image G1 which is a CT image has a higher CT value than that of the tissue of the human body. Thus, the first acquisition unit 22 acquires a stent region As1 from the three-dimensional image G1 by performing binarization processing for extracting a region having a CT value higher than a predetermined threshold value from the three-dimensional image G1. The first acquisition unit 22 acquires a stent region As2 from the three-dimensional image G2.

Figure 4:
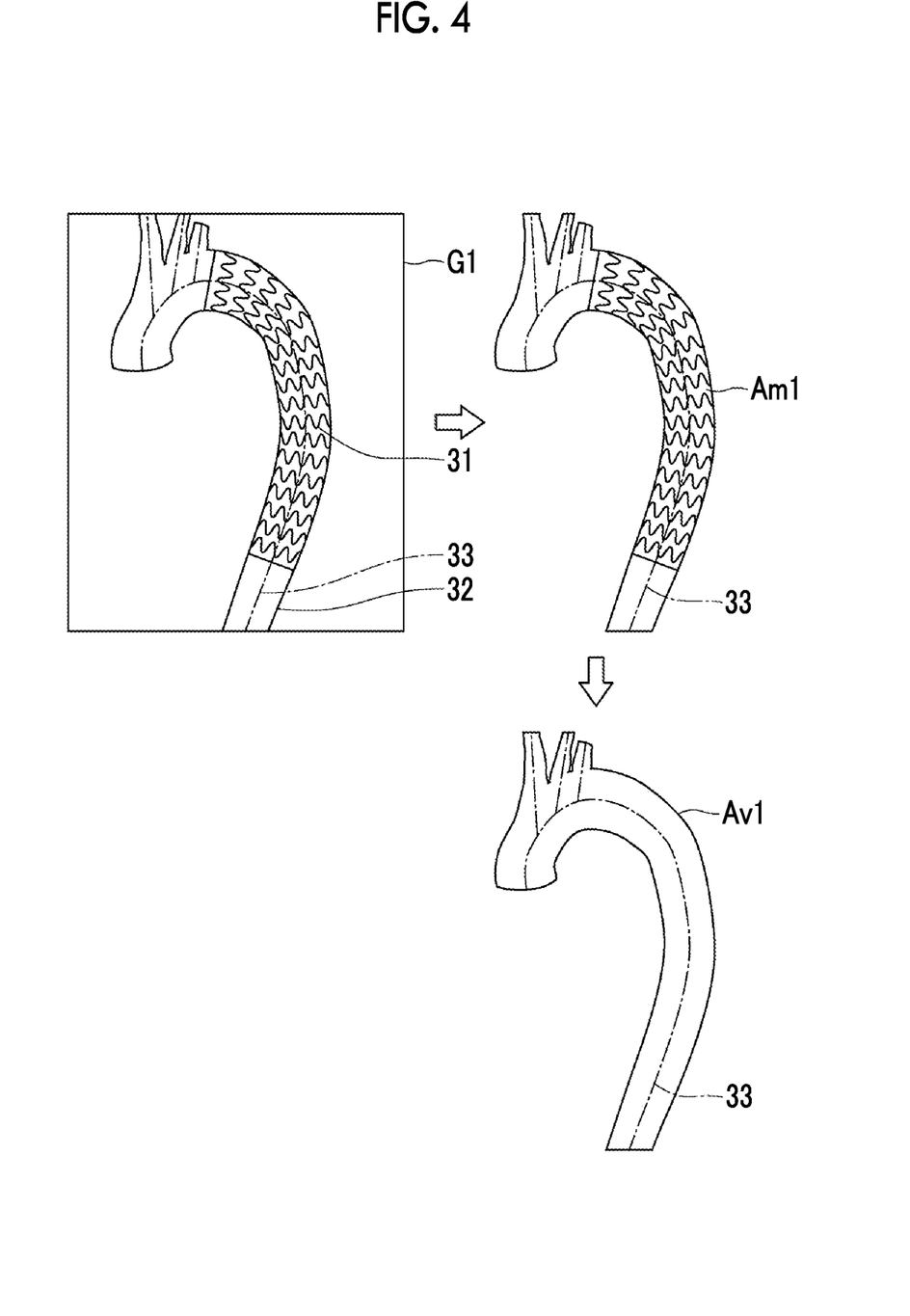
FIG. 4 is a diagram for describing acquisition of a blood vessel region.

The second acquisition unit 23 acquires a blood vessel region representing the blood vessel 32 moving in interconnection with the stent 31 from each of the two three-dimensional images G1 and G2. Specifically, regions including the stent 31 and the blood vessel 32 are acquired as interconnected regions Am1 and Am2 from the three-dimensional images G1 and G2, and acquires the blood vessel regions by removing the stent regions As1 and As2 from the interconnected regions Am1 and Am2. The blood vessel corresponds to the second structure, the blood vessel region corresponds to the second region, and the interconnected region corresponds to a third region.

FIG. 4 is a diagram for describing the acquisition of the blood vessel region. Here, since the acquisition of the blood vessel region is performed by the same processing in the three-dimensional images G1 and G2, the acquisition of the blood vessel region from the three-dimensional image G1 will be described.

The second acquisition unit 23 acquires the interconnected region Am1 including the stent 31 and the blood vessel 32 from the three-dimensional image G1 by a method described in, for example, JP 2010-200925 A and JP 2010-220742 A. In this method, first, positions of a plurality of candidate points constituting a core line of the blood vessel and a principal axis direction are calculated based on values of voxel data constituting the three-dimensional image G1. Alternatively, the positional information of the plurality of candidate points constituting the core line of the blood vessel and the principal axis direction are calculated by calculating a Hessian matrix for the three-dimensional image G1 and analyzing a specific value of the calculated Hessian matrix. Then, a feature value indicating the blood vessel, particularly, a blood vessel likeness is calculated for the voxel data around the candidate point, and it is determined whether or not the voxel data indicates the blood vessel based on the calculated feature value. The determination based on the feature value is performed based on an evaluation function acquired in advance by machine learning. Accordingly, the interconnected region Am1 and a core line 33 are extracted from the three-dimensional image G1. The core line 33 may be extracted by extracting the interconnected region Am1 first and performing thinning processing on the interconnected region Am1 region. The method of extracting the interconnected region and the core line is not limited to the aforementioned method, and any method can be used.

The second acquisition unit 23 acquires the blood vessel region Av1 by removing the stent region As1 acquired by the first acquisition unit 22 from the interconnected region Am1. Specifically, the interconnected region Am1 and the stent region As1 are positioned by subtracting a pixel value of the stent region As1 from the interconnected region Am1, and the pixel value of the stent region As1 is subtracted from a pixel value of the interconnected region Am1 between pixels corresponding to each other. Thus, the blood vessel region Av1 is acquired by removing a component of the stent region As1 from the interconnected region Am1. The second acquisition unit 23 acquires the blood vessel region Av2 by acquiring the interconnected region Am2 from the three-dimensional image G2 in the same manner as described above and further removing the stent region As2 from the interconnected region Am2.

Figure 5:
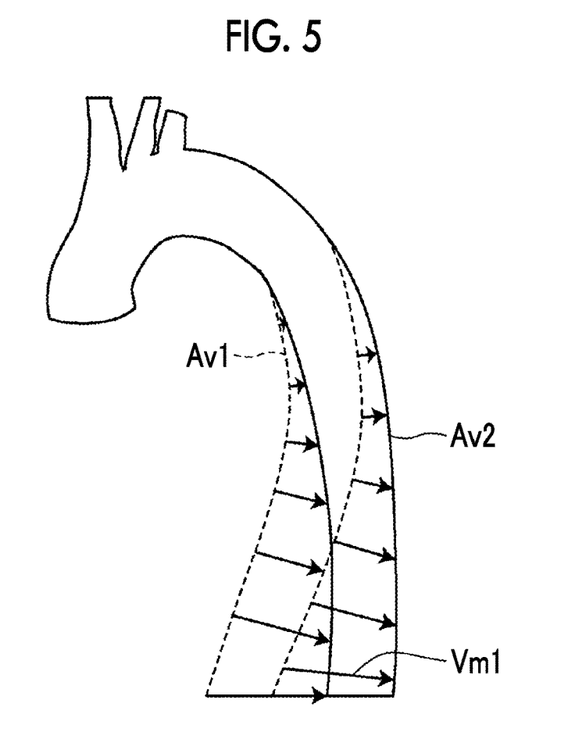
FIG. 5 is a diagram for describing acquisition of a first positioning result.

The positioning unit 24 acquires the first positioning result by positioning the blood vessel regions Av1 and Av2 for the three-dimensional images G1 and G2. In the present embodiment, a deformation vector Vm1 for matching each pixel position in the blood vessel region Av1 with a corresponding pixel position in the blood vessel region Av2 by performing non-rigid positioning such that the blood vessel region Av1 matches the blood vessel region Av2 is acquired as the first positioning result.

A method of converting each pixel position in the blood vessel region Av1 into the corresponding pixel position in the blood vessel region Av2 by using a function such as B-spline and thin plate spline can be used as the non-rigid positioning, but the present invention is not limited thereto.

FIG. 5 is a diagram for describing the acquisition of the first positioning result. In FIG. 5, the blood vessel region Av1 is indicated by a broken line, the blood vessel region Av2 is indicated by a solid line, and the deformation vector Vm1 is indicated by a solid line arrow. The deformation vector Vm1 is actually acquired for all the pixel positions in the blood vessel regions Av1 and Av2. However, only the deformation vector Vm1 for some pixel positions at contour lines in the blood vessel regions Av1 and Av2 is shown in FIG. 5 for the sake of simplicity in description.

Figure 6:
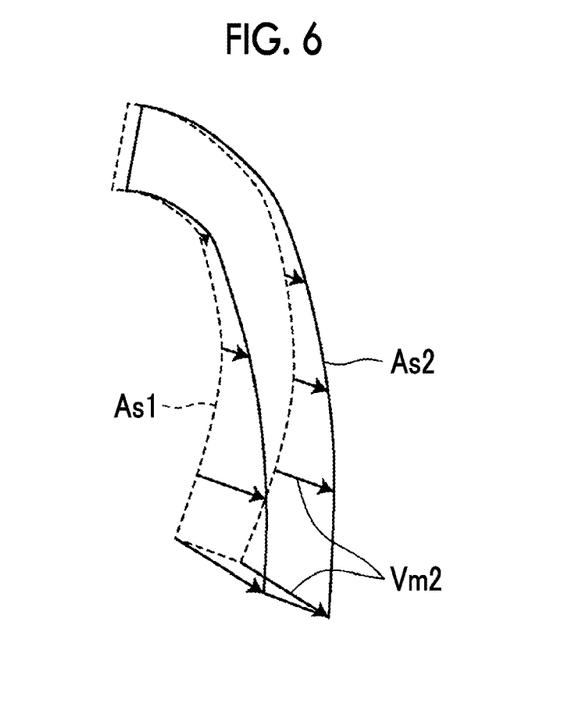
FIG. 6 is a diagram for describing acquisition of a second positioning result.
Figure 7:
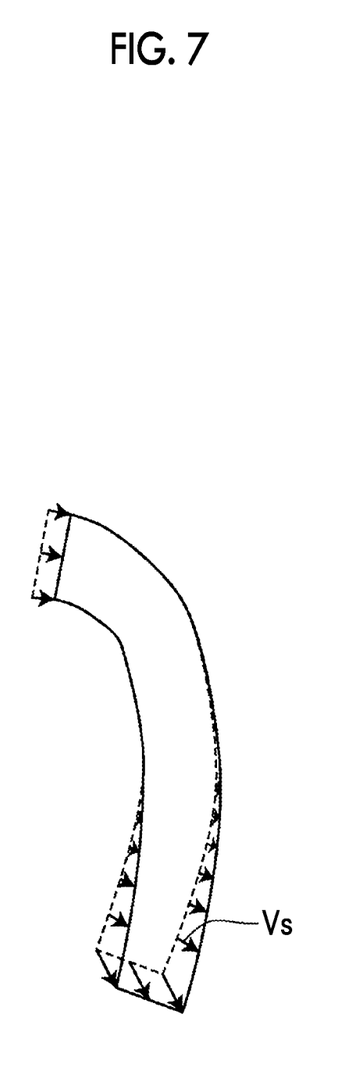
FIG. 7 is a diagram for describing acquisition of deviation information.

The deviation information acquisition unit 25 acquires the deviation information indicating the deviation of the stent 31 from the blood vessel 32 between the three-dimensional images G1 and G2 based on the stent regions As1 and As2 for the three-dimensional images G1 and G2 and the deformation vector Vm1 which is the first positioning result. Specifically, a second positioning result is acquired by positioning the stent regions As1 and As2 for the three-dimensional images G1 and G2 is acquired, and the deviation information is acquired by removing the component based on the first positioning result from the second positioning result. The deviation information includes the amount of movement of the stent 31 with respect to the blood vessel 32 and the amount of deformation of the stent.

First, the deviation information acquisition unit 25 acquires the second positioning result by positioning the stent regions As1 and As2 for the three-dimensional images G1 and G2. In the present embodiment, the deformation vector Vm2 for matching each pixel position in the stent region As1 with the corresponding pixel position in the stent region As2 is acquired as the second positioning result by performing the non-rigid positioning such that the stent region As1 matches the stent region As2.

FIG. 6 is a diagram for describing the acquisition of the second positioning result. In FIG. 6, the stent region As1 is indicated by a broken line, the stent region As2 is indicated by a solid line, and the deformation vector Vm2 is indicated by a solid line arrow. In FIG. 6, a mesh pattern of the stent is omitted. Although a deformation vector Vm2 is actually acquired for all the pixel positions in the stent regions As1 and As2, the deformation vector Vm2 for some pixel positions at contour lines in the stent regions As1 and As2 are shown in FIG. 6 for the sake of simplicity in description.

The deviation information acquisition unit 25 acquires the deviation information by removing the component based on the first positioning result from the second positioning result. Specifically, the component based on the first positioning result is removed from the second positioning result by subtracting the deformation vector Vm2 from the deformation vector Vm1 at the corresponding pixel position and calculating a difference vector Vs. The size of the calculated difference vector Vs is the deviation information. The deviation information acquired in this manner indicates the deviation of the stent 31 from the blood vessel 32 between the three-dimensional images G1 and G2, that is, the amount of movement and the amount of deformation of only the stent 31 by removing the influence of the position deviation of the blood vessel 32. FIG. 7 is a diagram showing the deviation information, that is, the difference vector Vs. As shown in FIG. 7, the deviation information, that is, the difference vector Vs indicates the amount of movement and the amount of deformation of the stent 31 between the three-dimensional images G1 and G2 by removing the influence of the position deviation of the blood vessel 32.

Figure 8:
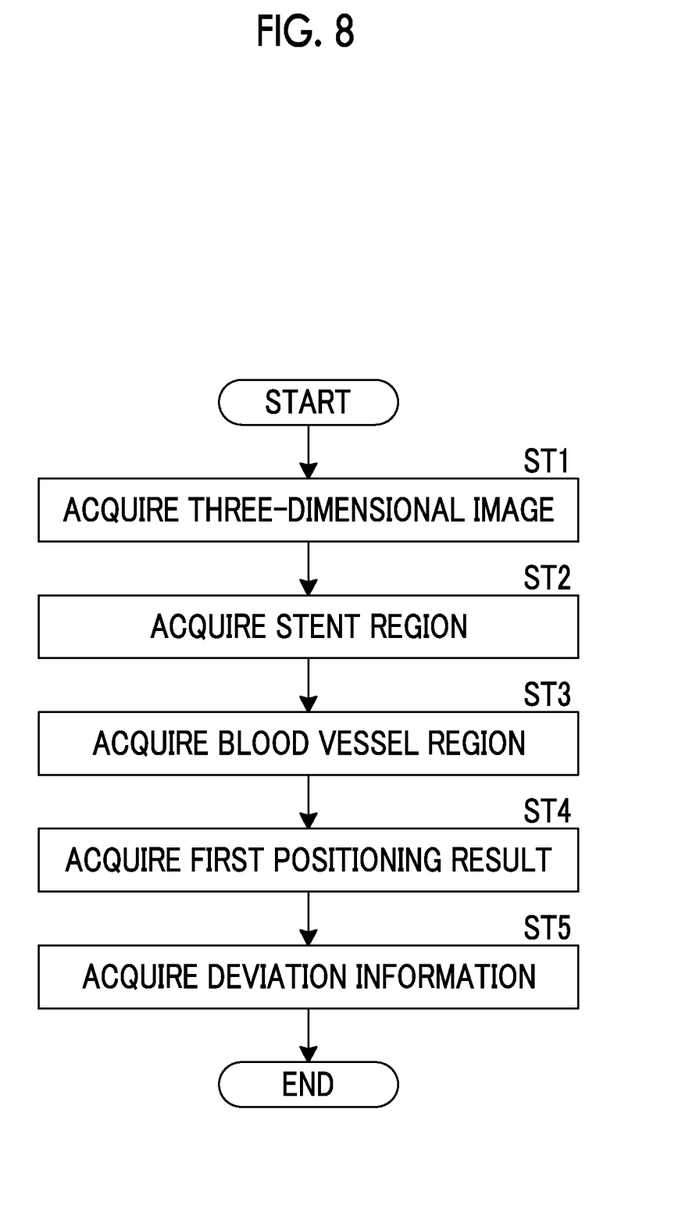
FIG. 8 is a flowchart showing processing performed in the present embodiment.

Next, processing performed in the present embodiment will be described. FIG. 8 is a flowchart showing processing performed in the present embodiment. First, the image acquisition unit 21 acquires the three-dimensional images G1 and G2 (step ST1), and the first acquisition unit 22 acquires the stent regions As1 and As2 from the three-dimensional images G1 and G2 (step ST2). Next, the second acquisition unit 23 acquires the blood vessel regions Av1 and Av2 from the three-dimensional images G1 and G2 (step ST3), and the positioning unit 24 acquires the first positioning result by adjusting the positions of the blood vessel regions Av1 and Av2 for the three-dimensional images G1 and G2 (step ST4). The deviation information acquisition unit 25 acquires the deviation information indicating the deviation of the stent 31 from the blood vessel 32 between the three-dimensional images G1 and G2 based on the stent regions As1 and As2 for the three-dimensional images G1 and G2 and the deformation vector Vm1 which is the first positioning result (step ST5), and the processing is ended.

As described above, in the present embodiment, the stent regions As1 and As2 and the blood vessel regions Av1 and Av2 are acquired from the three-dimensional images G1 and G2, the first positioning result is acquired by adjusting the positions of the blood vessel regions Av1 and Av2, and the deviation information indicating the deviation of the stent 31 from the blood vessel 32 between the three-dimensional images G1 and G2 based on the stent regions As1 and As2 and the first positioning result. Therefore, the deviation of the stent 31 from the blood vessel 32 can be detected.

In the aforementioned embodiment, the deviation information acquisition unit 25 acquires the second positioning result by positioning the stent regions As1 and As2 for the three-dimensional images G1 and G2, and acquires the deviation information by removing the component based on the first positioning result from the second positioning result. However, the stent region As1 for one three-dimensional image (here, the three-dimensional image G1) of the three-dimensional images G1 and G2 may be deformed based on the first positioning result, and the deviation information may be acquired based on the stent region As1 for the other three-dimensional image G2 and the deformed stent region As1. Since the deviation information acquired in this manner is equivalent to the deviation information acquired in the aforementioned embodiment, the deviation of the stent 31 from the blood vessel 32 can be detected as in the aforementioned embodiment.

In the aforementioned embodiment, the positioning unit 24 may acquire the first positioning result by positioning only the core lines of the blood vessel regions Av1 and Av2 for the three-dimensional images G1 and G2. Here, the position of the blood vessel deviates with time, but a diameter of the blood vessel is hardly changed. Thus, the deformation vector between the blood vessel regions Av1 and Av2 acquired by positioning the core lines is substantially equivalent to the deformation vector for all the blood vessel regions Av1 and Av2. Therefore, the first positioning result can be acquired by positioning the core lines of the blood vessel regions Av1 and Av2 with a small amount of calculation.

In a case where the first positioning result is acquired as described above, the deformation vector Vm1 is calculated only for each pixel position at the core line. Thus, for example, a plane orthogonal to each pixel position at the core line is defined for the deformation vector Vm1 at a pixel position other than the core line of the blood vessel region, and the same deformation vector as the deformation vector Vm1 at the pixel position at the core line is acquired as the first positioning result at the pixel position on this plane.

Although it has been described in the aforementioned embodiment that the deviation information for the stent 31 placed in the aorta is acquired, the blood vessel is not limited to the aorta as long as it is necessary to place the stent on the blood vessel. For example, the present embodiment can be applied to a case where deviation information of a stent placed in a coronary artery or a cerebral artery.

Although it has been described in the aforementioned embodiment that the CT image is used as the medical image, the present invention is not limited thereto, and may be an MRI image or a PET image.

Hereinafter, the operations and effects of the present embodiment will be described.

The core lines of the blood vessel are positioned, and the amount of calculation for acquiring the first positioning result can be reduced. Accordingly, the first positioning result can be quickly acquired.

What is claimed is:

1. A deviation detection device comprising at least one processor, wherein the processor is configured to:
   acquire a first region indicating a first structure as a deviation detection target between two medical images having different imaging times for the same test subject from each of the two medical images;
   acquire a second region indicating a second structure moving in interconnection with the first structure from each of the two medical images;
   acquire a first positioning result by positioning the second region for each of the two medical images; and
   acquire deviation information indicating a deviation of the first structure from the second structure between the two medical images based on the first region for each of the two medical images and the first positioning result.

2. The deviation detection device according to claim 1, wherein the processor is configured to acquire a third region including the first structure and the second structure from each of the two medical images, and acquires the second region by removing the first region from the third region in each of the two medical images.

3. The deviation detection device according to claim 1, wherein the processor is configured to acquire the first positioning result by non-rigid positioning.

4. The deviation detection device according to claim 1, wherein the processor is configured to acquire a second positioning result by positioning the first region for each of the two medical images, and acquires the deviation information by removing a component based on the first positioning result from the second positioning result.

5. The deviation detection device according to claim 4, wherein the processor is configured to acquire the second positioning result by non-rigid positioning.

6. The deviation detection device according to claim 1, wherein the processor is configured to deform the first region for one medical image of the two medical images based on the first positioning result, and acquires the deviation information based on the first region for the other medical image of the two medical images and the deformed first region.

7. The deviation detection device according to claim 1, wherein the medical image includes a blood vessel on which a stent is placed,
the first structure is the stent, and
the second structure is the blood vessel.

8. The deviation detection device according to claim 7, wherein the processor is configured to acquire the first positioning result by positioning a core line of a blood vessel region which is a region of the blood vessel for each of the two medical images.

9. A deviation detection method comprising:
   acquiring a first region indicating a first structure as a deviation detection target between two medical images having different imaging times for the same test subject from each of the two medical images;
   acquiring a second region indicating a second structure moving in interconnection with the first structure from each of the two medical images;
   acquiring a first positioning result by positioning the second region for each of the two medical images; and
   acquiring deviation information indicating a deviation of the first structure from the second structure between the two medical images based on the first region for each of the two medical images and the first positioning result.

10. A non-transitory computer-readable recording medium having stored therein a deviation detection program causing a computer to execute:
   a procedure of acquiring a first region indicating a first structure as a deviation detection target between two medical images having different imaging times for the same test subject from each of the two medical images;
   a procedure of acquiring a second region indicating a second structure moving in interconnection with the first structure from each of the two medical images;
   a procedure of acquiring a first positioning result by positioning the second region for each of the two medical images; and
   a procedure of acquiring deviation information indicating a deviation of the first structure from the second structure between the two medical images based on the first region for each of the two medical images and the first positioning result.

* * * * *